United States Patent [19]

Detroy

[11] 4,035,377

[45] July 12, 1977

[54] SLAB GEL ELECTROPHORESIS APPARATUS

[75] Inventor: Bruce A. Detroy, Huntington Station, N.Y.

[73] Assignee: Cold Spring Harbor Laboratory, Cold Spring Harbor, N.Y.

[21] Appl. No.: 589,464

[22] Filed: June 23, 1975

[51] Int. Cl.² ................................. G01N 27/26
[52] U.S. Cl. ...................... 204/299 R; 204/180 G
[58] Field of Search ................ 204/299, 180 G; 23/230 B, 253 R

[56] References Cited

U.S. PATENT DOCUMENTS

| | | | |
|---|---|---|---|
| 3,129,158 | 4/1964 | Raymond et al. | 204/180 G |
| 3,719,580 | 3/1973 | Roberts et al. | 204/299 |
| 3,822,197 | 7/1974 | Nees et al. | 204/180 G X |
| 3,856,655 | 12/1974 | Roberts | 204/299 |
| 3,879,280 | 4/1975 | Peterson et al. | 204/299 |
| 3,932,265 | 1/1976 | Hoefer | 204/299 |

*Primary Examiner*—Arthur C. Prescott
*Attorney, Agent, or Firm*—Brumbaugh, Graves, Donohue & Raymond

[57] ABSTRACT

Apparatus for vertical slab gel electrophoresis has upper and lower tanks having open tops. The tanks are supported in stepped relation to each other by a vertical support plate which forms a front wall of one tank and a rear wall of the other. At least part of the wall of the upper tank formed by the support plate has a top edge which is lower than the other top edges of the tank. A substantially open-ended chamber is formed by clamping a plastic plate to a glass plate with strip members between side edges of the plates. The plastic plate is held against the sport plate for reinforcing the rigidity of the plastic plate with the support plate. A portion of the top edge of the plastic plate is lower than the top edge of the glass plate and intermediate the lower edge portion of the wall of the upper tank formed by the support plate and the other top edges of the upper tank. Partitions extend across the chamber from the plastic plate to the glass plate and down into the chamber from the top, lower edge of the plastic plate at least to a slab of gel which fills the chamber to form wells over the gel for receiving samples. An electrolytic buffer solution is placed in both tanks, the solution in the upper tank flowing over the lower edges of the support plate and plastic plate to the glass plate to cover the samples in the wells. Opposite electric potentials of the appropriate polarity are then applied to electrodes in both tanks to cause the samples to migrate electrophoretically into the gel, the position of the samples in the gel then being an indication of the composition of the samples.

5 Claims, 5 Drawing Figures

SLAB GEL ELECTROPHORESIS APPARATUS

BACKGROUND OF THE INVENTION

The invention described herein was made in the course of work under a grant from the Department of Health, Education and Welfare.

Electrophoresis is a process in which an electric field applied across a medium causes particles of samples on the medium which have an associated electric charge to migrate into the medium. The extent of migration is an indication of the composition of the particles. Proteins, viruses, clay suspensions, rubber emulsions, colloidal particles, enzymes such as those which cause physical changes in deoxyribonucleic acid (hereafter DNA), and fragments of DNA molecules are a few examples of the many substances having particles of the appropriate size and associated charge for migration and consequent assay by electrophoresis.

Both horizontal and vertical types of electrophoresis apparatus are known. One type of horizontal apparatus has a sheet of paper forming a capillary mesh medium. The paper extends substantially horizontally between two tanks filled with an electrolytic buffer solution. A potential is applied to electrodes in each tank and a sample is placed on the paper intermediate the tanks. The electric field extending through the paper then causes the sample to migrate along the paper, the extent of migration being an indication of the composition of the sample.

One type of known vertical electrophoresis apparatus has a support plate which forms one inner wall of an upper tank and an opposite inner wall of a lower tank. The support plate alos supports the tanks in stepped relation to each other. Both tanks have open tops. At least a portion of the top edge of the support plate is lower than the top edges of the other walls of the upper tank. A slab of agarose gel is formed in and supported by an open-ended chamber which comprises two glass plates which are spaced from each other by strip members extending between and along their side edges. A top edge of one plate is aligned approximately with and sealed to the lower top edge portion of the upper tank. The top edge of the other plate on the other side of the slab of gel extends above the lower edge portion of the upper tank and other plate to retain an electrolytic buffer solution which fills the upper tank to a level at which it flows over the lower edges of the tank and plate to cover the gel between the plates. The glass plates and the gel therebetween extend vertically along the support plate into the lower tank which is also filled with an electrolytic buffer solution. Electrodes in each tank carry opposite electric potentials of a polarity appropriate for causing a sample placed between the glass plates on top of the gel to migrate into the gel.

In one mode of operating this vertical electrophoresis apparatus, a comb is inserted into the top portion of the gel to form a discrete well in the gel with each tooth of the comb. Individual samples are then placed in each well to simultaneously assay each of the samples with the electrophoresis process. In order to individually assay each of the samples, the wells must keep each sample separate from the samples in adjoining wells.

Experience has shown that it is difficult to form such discrete wells with a comb projecting into the gel. The gel does not adhere well to the plates so that, particularly as the comb is withdrawn from the gel, the gel between adjacent teeth of the comb tends to rupture and tear thereby destroying the integrity of the wells formed by the adjacent teeth of the comb.

Inasmush as the extent of migration of samples in the wells is important to the assay of the samples, it is also important to know precisely the initial depths of the wells for determining the initial position of the samples in the wells. It is also most convenient for comparing several samples if the wells have a uniform depth so that the initial position of each sample does not have to be determined individually. To assure such uniform depths to the wells, it is necessary both to accurately position the comb in the gel and to check each well after removing the comb to discover if pieces of the gel which may tear from sides of the wells have slid down to partially fill the bottoms of individual wells.

The relatively poor adherence of the gel to the plates also requires that the plates rigidly support the gel so that flexing of the plates does not permit the gel to slide down between the plates. If the gel were to slide between the plates after the initial position of a sample on top of the gel is determined, the initial position of the sample would change thereby making inaccurate measurement of the extent of migration of the sample by electrophoresis from the initial and final position of the sample in the gel. Known apparatus has used double window strength glass plates approximately 3mm. thick for rectangular plates only 14 cm. by 16 cm.

The vertical electrophoresis apparatus described above has been modified to overcome the problem of producing discrete, uniform wells in the gel with a comb which penetrates the gel by providing a third plate between the two glass plates forming the chamber for the gel. The third plate extends along and is supported by the glass plate which is remote from the support plate. The third plate has partitions which extend down the plate to the gel and extend across the chamber to the other glass plate to form individual wells for receiving individual samples. To assure that the partitions extend down to the gel to seal the bottom of each well with the gel, a comb having teeth which closely fit between each partition is inserted before the chamber is filled with gel. The chamber is inverted and filled with a liquid which forms the gel. The liquid which forms the gel then runs down to the cooperative ends of the partitions and the comb but does not substantially run between the partitions and teeth of the comb because of the snug fit therebetween. After the liquid gels, the plates are reinverted. The lower end of each partition is then sealed in the gel and, there being substantially no gel between the partitions, gel is not torn from the sides of the wells as the comb is removed from between the partitions. Each well then also has a depth which accurately extends to the bottom of the partitions.

The tolerance between the partitions and the teeth of the comb necessary to prevent leakage of the liquid forming the gel between the partitions and the teeth must average ± 0.002 inch (0.005 cm), but not exceed an accumulated tolerance of ± 0.010 inch (0.025 cm.) for all of the sample wells, about 20 sample wells across about 6¼ inches (15.8 cm.) being one example. (Inasmuch as the comb is a mating part, the accumulated tolerance across the comb must be in the same direction as that across the partitions.)

The close tolerances required for the partitions would suggest using a rigid material. The partitions, however, must also seal themselves to the opposite glass plate to maintain the integrity of the wells. Such sealing is easiest to obtain if the partition material has some resilience.

The third plate and partition material also must be electrically non-conductive so as to maintain the electric field through the gel. The third plate preferably is transparent for convenience in determining the extent of migration of the samples from the front of the apparatus (i.e., through the one glass plate and the third plate which is supports).

One material suitable for the third plate and its partitions is a polycarbonate plastic available under the name Lexan from General Electric Company. This material, however, does not have sufficient rigidity in thicknesses of about ⅛ inch (0.3 cm.), which are desired for forming the chamber without unnecessary bulk, for adequately holding the gel without slippage. It therefore has been necessary to back the plastic plate with the glass plate, thereby requiring the three plates for forming the chamber.

In addition to the undesirable bulk and complexity introduced by having three plates form the chamber for the gel, it has also been found that side ends of the one glass plate which desirably extend above the lower portion of its top edge for sealing the plate to the upper tank at sides of the plate are easily broken off. Once the side ends or ears of the one glass plate break, the plate will not seal to the upper tank and thus cannot be used. The glass plate cannot be removed from the gel without destroying the integrity of the gel. Considerable delay in the assay of samples then results from the necessity to prepare a new gel between unbroken plates.

SUMMARY OF THE INVENTION

It is an object of the invention to provide an improved vertical electrophoresis apparatus in which the unnecessary bulk and complexity of having three plates form the chamber for the gel is avoided, but the rigidity of the chamber retained so as to adequately hold the gel in the chamber. It is a further object of the invention to eliminate the raised sides or ears of one glass plate which heretofore have often broken to delay assay of samples until a new gel for the electrophoresis process could be prepared between unbroken plates.

The invention provides apparatus for vertical slab gel electrophoresis in which an upper tank is supported in stepped relation to a lower tank by a support plate. The support plate also forms two of the inner walls of the tanks. At least part of the inner wall of the upper tank which is formed by the support plate has a top edge which is lower than the top edges of the other walls of the upper tank.

A substantially open-ended chamber for containing and supporting a slab of gel comprises a substantially rigid plastic plate, a rigid glass plate, and strip members between side edges of the plates. The plastic plate is held against the support plate for reinforcing the rigidity of the plastic plate, the glass plate on the other side of the gel being sufficiently rigid to support the gel. Holding the plastic plate against the support plate also seals the plastic plate to the support plate along the lower top edge part of the support plate.

A portion of the top edge of the plastic plate is intermediate the lower edge part of the inner wall of the upper tank formed by the support plate and the edges of the other walls of the tank, but the top edge of the glass plate extends above this lower edge portion of the plastic plate. Means, such as side portions of the plastic plate, extend above the lower edge portion of the plastic plate at the sides of the plastic plate to seal the upper sides of the plastic plate to the upper tank.

Parallel partitions extend inwardly from the plastic plate across the chamber to the glass plate at the lower edge portion on the top of the plastic plate and extend downwardly from the lower edge portion of the plastic plate at least to the slab of gel which fills the chamber between the plates. The gel seals the bottom of the space between each pair of partitions to form individual wells for receiving individual samples to be assayed in the apparatus.

With samples in the wells over the gel and the plates held against the support plate, as by a clamp, for reinforcing the rigidity of the plastic plate and sealing the plastic plate to the support plate, both the upper and lower tanks are filled with an electrolytic buffer solution. The solution in the upper tank flows over the lower edge portions of the support plate and plastic plate to cover the samples in the wells, but is retained in the upper tank by the higher edge of the glass plate and the sealing means at the side edges of the plastic plate. Opposite electric potentials of appropriate polarity are then applied to an electrode in each tank. The electrolytic buffer solution applies the electric potential to opposite ends of the gel for creating an electric field through the gel. The electric field causes particles with an associated electric charge in the samples to migrate from the wells into the gel. The extent of migration of the particles is an indication of their composition.

A convenient way of filling the chamber between the plates with the gel so that the gel seals the bottoms of the wells between the partitions to a substantially uniform level for readily but accurately determining the initial position of each sample, first assembles the plates to form the chamber before mounting the plates on the support plate of the apparatus. Teeth of a comb which fit snugly between the partitions are inserted between the partitions and the plates and comb then inverted for receiving a liquid which forms the gel. The liquid runs down to and seals the spaces between the ends of the partitions but does not extend into the wells between the partitions which are substantially filled by the snugly-fitting teeth of the comb. After the gel has formed, the plates are reinverted and the comb removed to expose the wells between the partitions which now are sealed at their lower ends by the gel.

After the gel forms, the plates must be handled carefully so that flexure of the plates, particularly the plastic plate, does not dislodge the gel. Once the plates are mounted in the apparatus with the plastic plate held against the support plate, the support plate reinforces the rigidity of the plastic plate to prevent flexure of the plastic plate enough to permit the gel to slide between the plates away from the partitions. If the gel slides away from the partitions, it will no longer seal the ends of the wells between the partitions and the integrity of the wells and the discrete samples therein has been lost.

The relatively brief careful handling of the plates before the plastic plate is held against and reinforced by the support plate is a modest disadvantage as compared to the problems presented by forming wells in the gel without partitions between the plates. The rigid partitions avoid the problem of rupturing the gel between individual wells upon removing a comb with which the wells were formed in the gel. Because the partitions and not the gel form the sides of the wells, portions of the gel also cannot be torn from the sides of the wells, the loose portions of gel then falling into the bottom of the wells to provide a non-uniform initial position to samples later placed in the wells.

The careful handling of the plates before the rigidity of the plastic plate is reinforced by the support plate is also a modest disadvantage as compared to the difficulty of assembling and manipulating three plates for forming the chamber which supports the gel. Two outer plates were then made of glass to provide rigid support for the gel. An intermediate plastic plate was supported by one glass plate and had partitions extending across the chamber to the other glass plate. The three plates first had to be assembled and securely clamped together while the chamber between two of the plates was filled with the gel. If a plate adjacent the gel slid relative to the other plate contacting the gel, the gel could be torn from the partitions to destroy the integrity of the wells between the partitions. Inasmuch as only the two outer glass plates could be held, the third plate only being pressed between the other two, there was considerable risk of the third plate sliding relative to the glass plate on the other side of the gel. In addition, the two glass plates which provided the structural rigidity necessary for supporting the gel could be broken easily, particularly at side portions or ears of the one plate which sealed the chamber to the upper tank.

Each of these disadvantages is avoided by the structure described herein. The partitions extending from the plastic plate for forming wells cannot be torn or ruptured upon removing a comb used in forming the wells. By having only two plates form the chamber for holding the gel, each plate may be held against slippage while moving the plates and gel into the apparatus. Once the two plates are positioned in the apparatus, the rigidity of the plastic plate is reinforced by the support plate and the plastic plate, although less rigid than glass, is not as subject to breakage at, particularly, side portions or ears for retaining the electrolytic buffer solution in the upper tank at sides of the plastic plate.

DESCRIPTION OF THE DRAWINGS

The preferred embodiment of the invention, which is intended to illustrate and not to limit the invention, will now be described with reference to drawings in which.

DESCRIPTION OF THE PREFERRED EMBODIMENT

Figure 1:
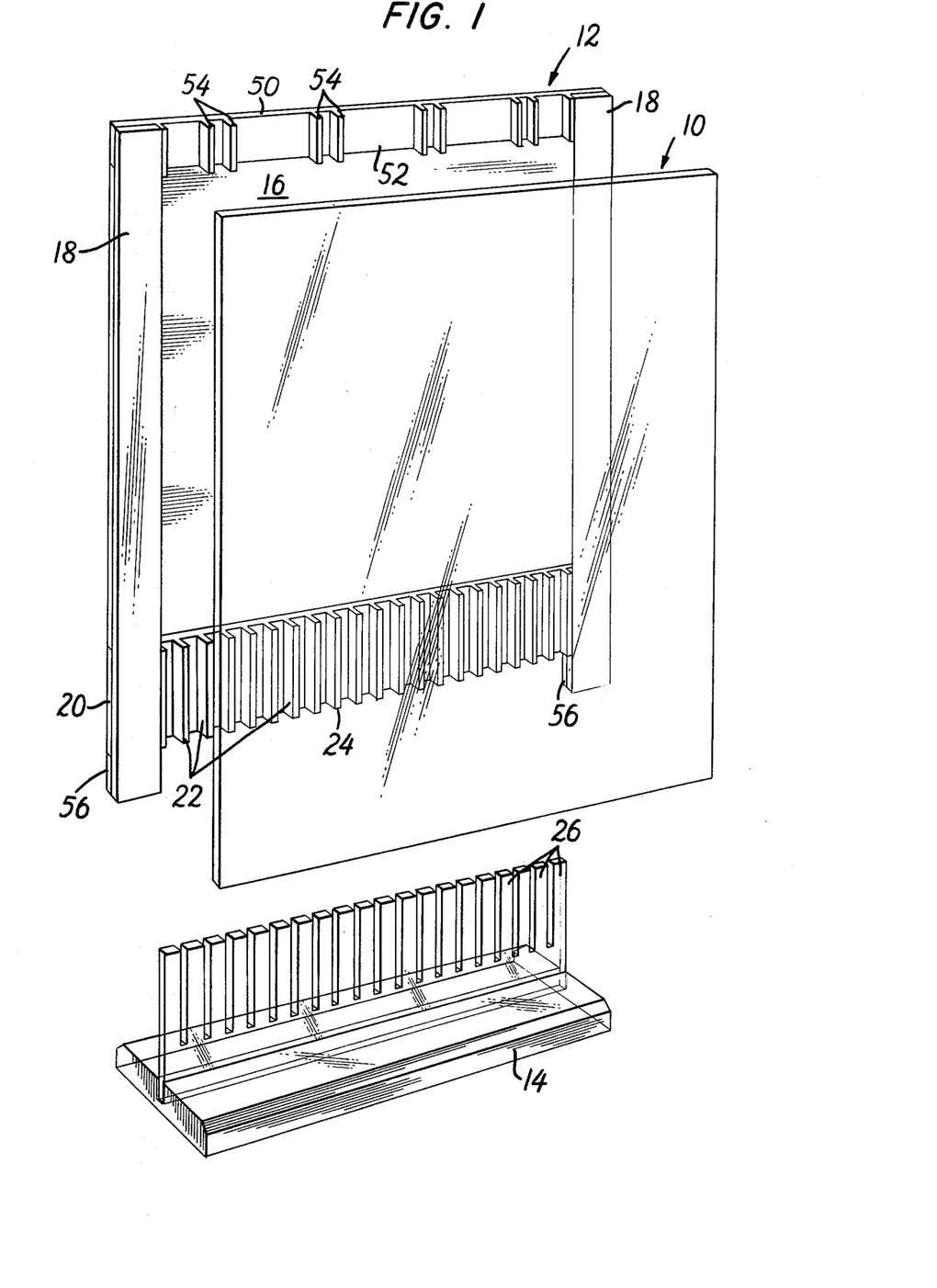
FIG. 1 is an exploded, three dimensional view of the plates and a comb which form the chamber in which the gel is formed.

Plates 10, 12, which form a chamber in which a slab of gel is formed, are shown in FIG. 1 with a comb 14 which assists in forming the slab of gel within the chamber. The plate 12 is formed from several preassembled pieces, the principal ones of which are a generally flat central plate portion 16, strip members 18 extending along side edges of the plate 12 for spacing the plates to form the chamber which will contain the gel, and a portion 20 having partitions 22 which extend parallel to the side edges of the plate from an indented edge portion 24.

Figure 2:
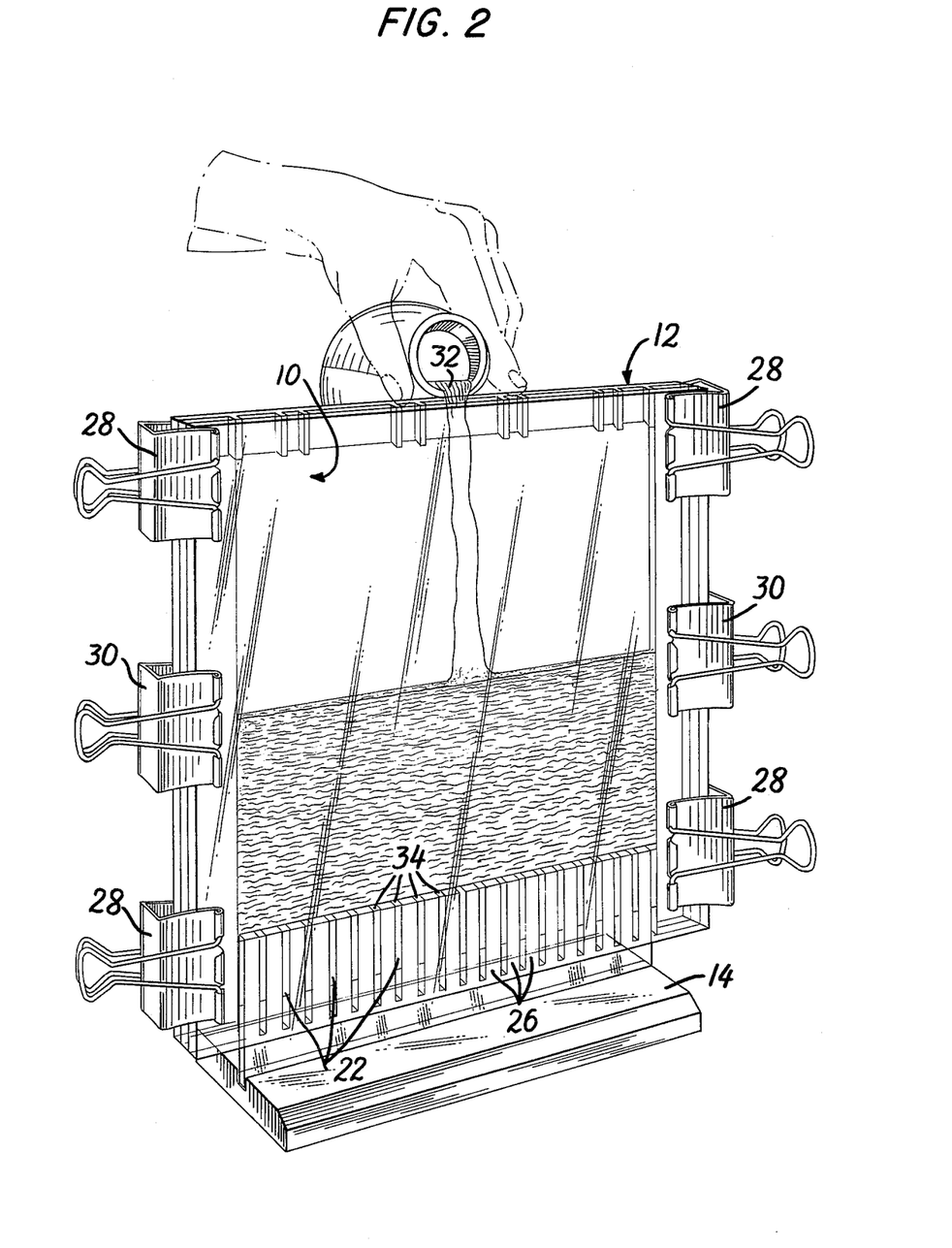
FIG. 2 is a view of the plates and comb shown in FIG. 1 assembled for forming the gel.

As seen in FIG. 2, the partitions 22 extend across the chamber between the plates and cooperatively fit between teeth 26 of the comb 14 for sealing the end of the chamber when the plates are held together with clamps 28, 30. A liquid 32 which forms the gel is then poured into the chamber between the plates. The liquid runs down to end portions 34 of the partitions which are substantially aligned with ends of the teeth of the comb for sealing the space between the ends of the partitions with the gel. The plates as shown in FIGS. 1 and 2 have been inverted from their normal orientation for forming the gel.

Figure 3:
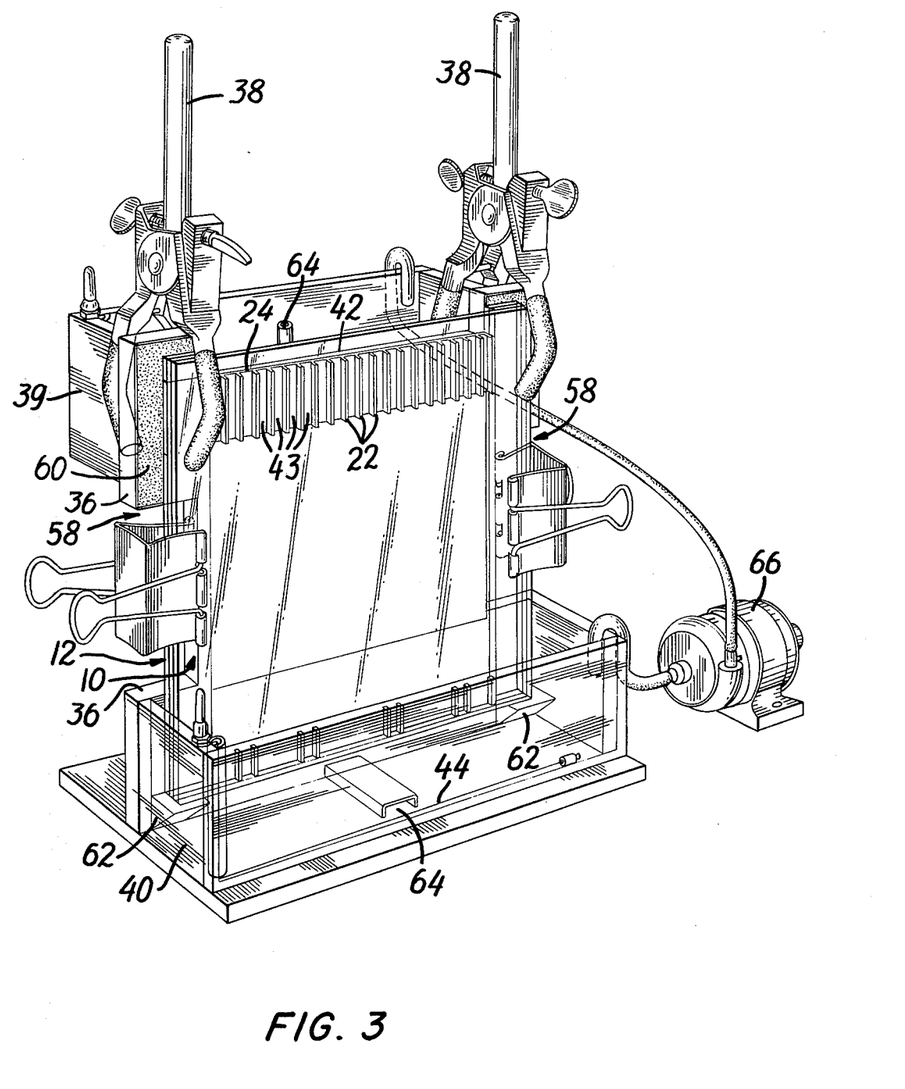
FIG. 3 is a three dimensional view showing the plates assembled with the rest of the embodiment after the formation of the gel.

As shown in FIG. 3, the plates then are reinverted, the comb 14 removed, and the plates, with the gel in the chamber therebetween, held against a support plate 36 by clamps 38 with the plastic plate 12 against the support plate for reinforcing the rigidity of the plastic plate with the support plate. The support plate 36 forms opposite front and rear inner walls of upper and lower tanks 39, 40, respectively, and supports the tanks in stepped relation.

The indented end portion 24 of the plastic plate is intermediate the top of plate 10 and a port 42 of the edge of the inner wall of the upper tank formed by the support plate 36 which is lower than the top edges of the other walls of the upper tank. The sides of the plastic plate 12 adjacent the portion 24 extend above the lower edge of portion 24 for retaining an electrolytic buffer solution (not shown) with which both the upper and lower tanks are filled, the upper tank being filled to a level at which the solution extends over the lower edge portions 24, 42 of the plate and tank for communicating with wells 43 formed by the partitions 22 on top of the gel.

Figure 4:
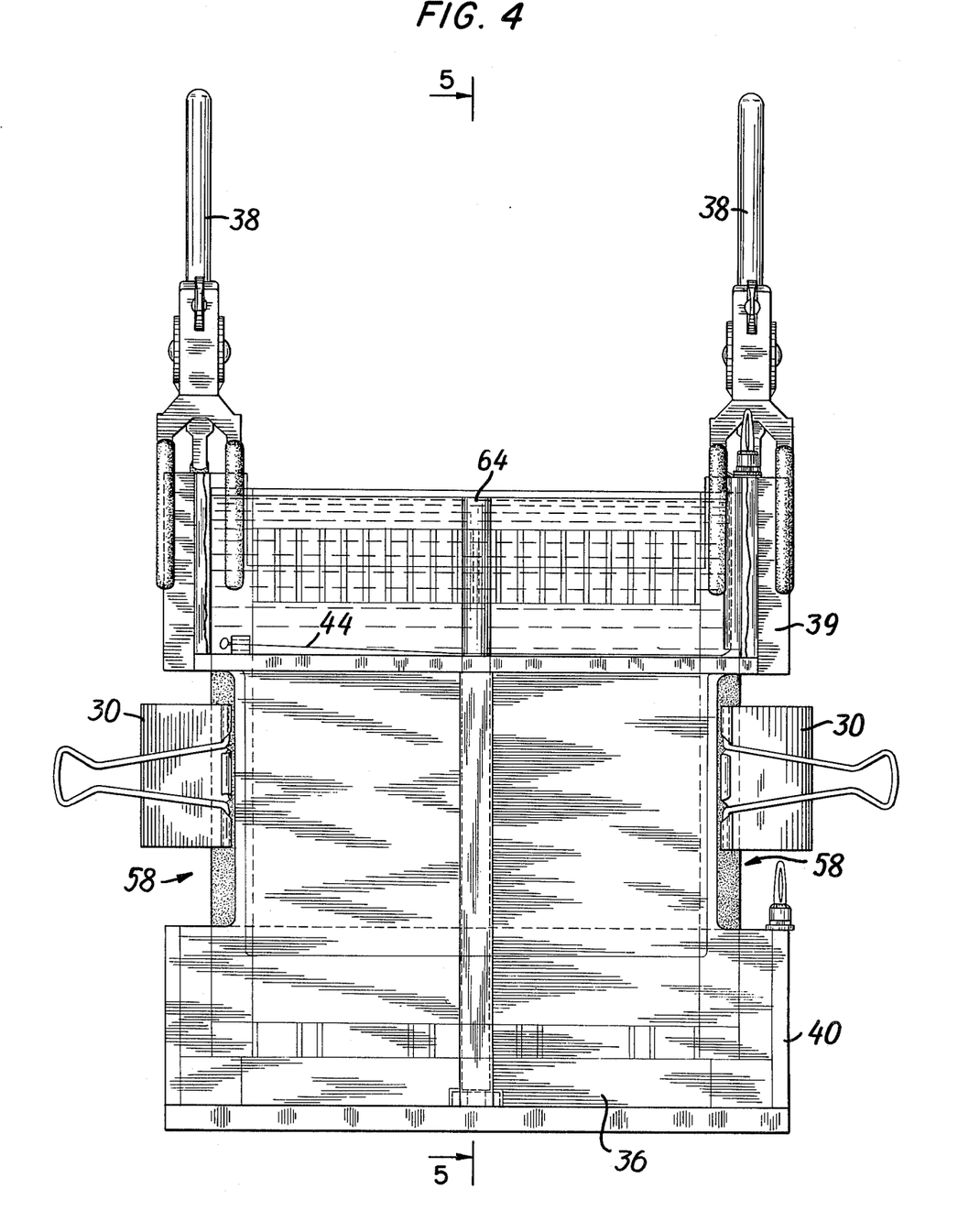
FIG. 4 is a rear elevation of the apparatus shown in FIG. 3.

Opposite electric potentials of appropriate polarity are then applied to an electrode 44 in each tank (the electrode in the upper tank being shown in FIG. 4). The electrolytic buffer solution applies the electric potential to opposite ends of the gel for creating an electric field (preferably about 6 v/cm.) through the gel. The electric field causes samples having particles with an associated electric charge to migrate from the wells 43 into the gel. The extent of migration of the samples in the gel is an indication of the composition of the samples.

MORE DETAILED DESCRIPTION OF THE PREFERRED EMBODIMENT

Returning to FIG. 1 for a more detailed description of the preferred embodiment, it will now be appreciated that at least one of the plates 10, 12 must be transparent to the means which detect at least the final position of the samples in the gel. Preferably, both plates are transparent to light so that optical means may be used for locating the initial and final positions of the samples in the gel. Plate 10 is therefore made of glass. The glass must be about 3/16 inch (0.475 cm.) thick to have sufficient rigidity to adequately support the gel between the plates over the entire area of the plates which are about 7.5 inches × 8 inches (19 cm. × 20 cm.) in the illustrated preferred embodiment.

Plate 12, however, is preferably formed from a transparent polycarbonate plastic such as Lexan which is available from the General Electric Company. The several pieces of plate 12 then may be assembled with dichloromethane to seal each piece to the others. Each portion of plate 12, for example plate portion 16, is preferably ⅛ inch (0.32 cm.) thick, the plate having overall dimensions generally corresponding to plate 10. Edges of the plate 12 receive the strip members 18 which are also ⅛ inch (0.32 cm.) thick for spacing the plates from each other to form the chamber for the gel and for reinforcing the plate.

One end of plate 12 (the top as shown in FIG. 1, but the bottom as shown in FIG. 3) has a member 50 which has been milled to have relatively wide regions 52, which are as thick as the plate portion 16, spaced by projections 54, which are as deep as the strip members 18, fo accurately spacing the end of the plate 12 from plate 10 when the plates are assembled for receiving the gel. The other end of plate 12 carries the member 20 in which the partitions 22 have been milled. The member 20 has a thickness between the partitions equal to that of the plate portion 16, and the partitions 22 have a depth equal to strip members 18 so that they extend across the chamber between the plates to sealingly engage the plate 10 for forming the individual wells which receive the samples to be assayed. Small seal members 56 extend along portions of the strip members 18 which extend beyond the member 20. The members 56 are again as thick as the plate portion 16 so as to form a smooth surface on plate 12 for sealingly engaging the support plate 36 (FIG. 3).

The liquid 32 (FIG. 2) which forms the gel is preferably prepared by boiling agarose (0.5% to 1.4%) in a buffer solution containing 0.04M tris-acetate (pH 7.9), 0.005M sodium acetate, and 0.001M sodium ethylene diamene tetra-acetic acid ($Na_2$ EDTA). The liquid is then cooled to room temperature and forms the gel. After cooling the liquid to 60° C but before pouring it into the chamber, ethidium bromide (0.5 micrograms per ml) may be added.

The gel filled chamber is then inverted and mounted in the apparatus as shown in FIG. 3 so that the ends of the gel are in fluid contact with the electrolytic buffer solution in the upper and lower tanks. The bottom of the plates is supported on projections 62 at either side of the lower tank for exposing the bottom of the gel to the electrolytic buffer solution in the lower tank.

The clamps 28 are removed from the ends of the plates, but the clamps 30 continue to hold the plates together, the clamps 30 being accomodated by recesses 58 in the sides of the support plate 36. A thin, resilient gasket 60 is placed between the support plate and the plastic plate at the upper tank for sealing the plastic plate to the upper tank at the lower edge portion 42 of the tank. The gasket is sufficiently thin so that its resiliency, although sealing the plastic plate to the support plate, does not permit such substantial flexure of the plastic plate as would permit the gel to slip between the plates.

An overflow passage 64 extends from a level above the intermediate edge portion 24 of the plastic plate to the lower tank. A pump 66 communicates with the lower tank at a level above the bottom of the gel for withdrawing buffer solution from the lower tank and carrying the solution to the upper tank. The overflow passage 64 and pump 66 thus cooperate to continuously circulate the buffer solution between the upper and lower tanks.

Figure 5:
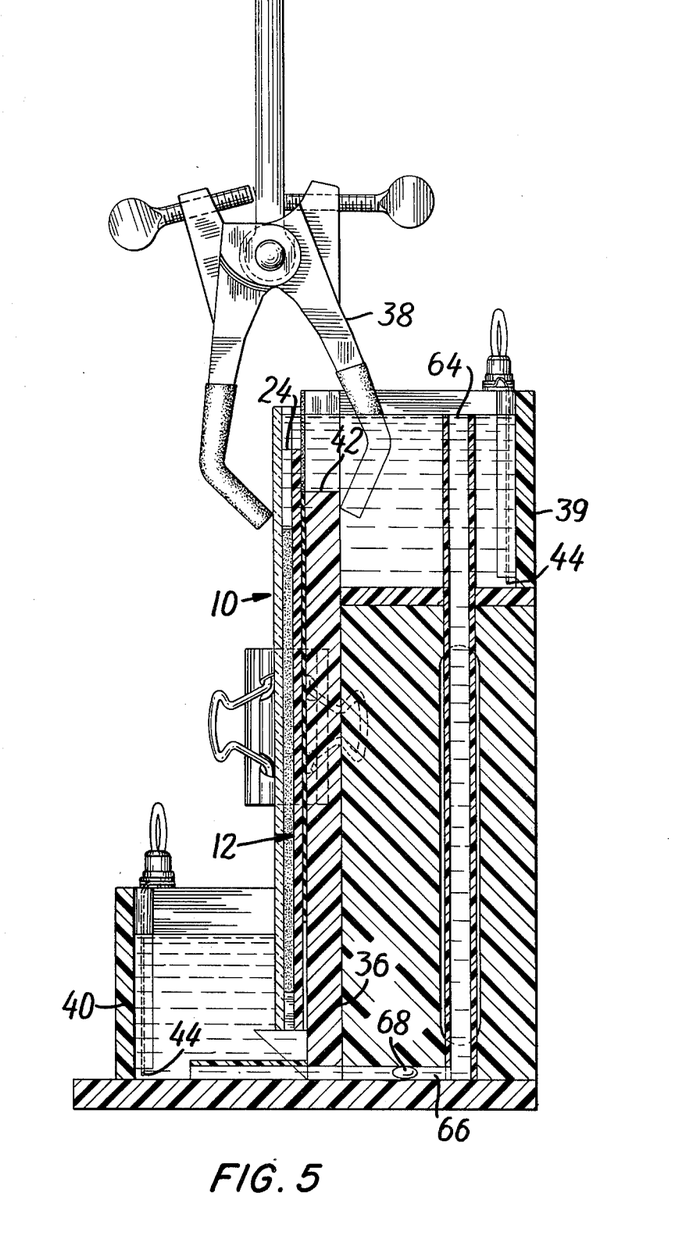
FIG. 5 is a side elevation, partly in section, of the apparatus shown in FIG. 3.

As best seen in FIG. 5, a portion 66 of the overflow passage 64 which carries the buffer solution into the lower tank retains an air bubble 68 for preventing the flow of electricity through the electrolyte in the overflow passage 64. At least the plates 10, 12, and 36 are also electrically non-conductive. The potential which is applied to the electrodes 44 then creates the electric field through the gel.

The plastic plate 12 may be made from any thermoforming or thermosetting material which is sufficiently rigid to adequately support the gel before the rigidity of the plastic plate is reinforced by its engagement with the support plate (through gasket 60). Other modifications to the invention described herein as will occur to those having skill in the appropriate arts are contemplated within the scope of the invention, in which

I claim:

1. Vertical slab gel electrophoresis apparatus which is particularly useful with agarose gel, the apparatus comprising: upper and lower oppositely extending tanks; a vertical support plate forming an inner wall of each tank and supporting the tanks in stepped relation, at least part of the top edge of the inner wall of the upper tank which is formed by the support plate being lower than other top edges of the upper tank; an electrode in each tank; a substantially rigid plastic plate with one side adjacent the support plate; strip members along opposite side edges of the other side of the plastic plate; a rigid glass plate clamped to the plastic plate and spaced therefrom by the strip members for forming a substantially open-ended chamber between the plates for receiving the slab of gel; parallel partitions extending from the plastic plate across the chamber and down the plastic plate from the top edge thereof to the gel for forming wells, the portion of the top edge of the plastic plate having the partitions being intermediate the lower edge part of the inner wall of the upper tank formed by the support plate and the top edges of the other walls of the upper tank, and the top edge of the glass plate being higher than the top edge of the plastic plate; means for clamping said plates together; and means removably holding the plastic plate against the support plate for reinforcing the rigidity thereof with the support plate and for sealing the plastic plate to the support plate, whereby the gel may be formed in the chamber while the chamber is inverted with teeth of a comb between the partitions and before the rigidity of the plastic plate is reinforced by its sealing contact with the support plate, the chamber then turned upright, the comb removed and the rigidity of the plastic plate reinforced by contact with the support plate to keep the gel from slipping so that samples may be placed in the wells formed between the partitions at the top of the gel and the tanks filled with an electrolytic buffer solution which flows over said inner wall and intermediate plate edges from the upper tank to the wells for the electrophoretic assay of the samples.

2. Apparatus as set forth in claim 1 wherein the plastic plate has several portions each of which is a polycarbonate about ⅛ inch (0.32 cm.) thick for making the plastic plate sufficiently rigid to prevent the gel from slipping in the chamber until the plastic plate is held against the reinforcing support plate, the gel being formed in the chamber before the plastic plate is held against the support plate, and for providing a flat surface to the plastic plate which seals to the support plate.

3. Apparatus as set forth in claim 1 and additionally comprising a gel in the chamber, the gel being formed from only agarose in a concentration of from 0.5% to 1.4% in a buffer solution.

4. Apparatus as set forth in claim 2, wherein the plastic plate has sufficient rigidity to prevent the agarose gel from slipping in the chamber until the plastic plate is held against the support plate to reinforce its rigidity.

5. Apparatus as set forth in claim 4 wherein the buffer solution contains 0.4M tris-acetate (7.9 pH), 0.005M sodium acetate, and 0.001M $Na_2$ EDTA.

* * * * *

UNITED STATES PATENT AND TRADEMARK OFFICE
CERTIFICATE OF CORRECTION

PATENT NO. : 4,035,377
DATED : July 12, 1977
INVENTOR(S) : Bruce A. DeTroy

It is certified that error appears in the above-identified patent and that said Letters Patent are hereby corrected as shown below:

First page, Heading and Item (75), "Detroy" should be -- DeTroy --;
First page, Col. 2, line 9, "spport" should be -- support --;
Col. 1, line 34, "alos" should be -- also --;
Col. 2, line 3, "Inasmush" should be -- Inasmuch --;
Col. 3, line 9, "is" should be -- it --;
Col. 7, line 13, "fo" should be -- for --;
Col. 9, line 1, "claim 2" should be -- claim 3 --;
Col. 10, line 3, "claim 4" should be -- claim 3 --;
Col. 10, line 4, "0.4M" should be -- 0.04M --.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks